United States Patent [19]

Pugach et al.

[11] Patent Number: 5,567,838
[45] Date of Patent: Oct. 22, 1996

[54] TRANSESTERIFICATION REACTION OF ALKOXYLATED BISPHENOL-A AND METHYL METHACRYLATE

[75] Inventors: Joseph Pugach, Monroeville; Jeffrey S. Salek, Oakdale; John E. Aiken, Monroeville, all of Pa.

[73] Assignee: Aristech Chemical Corporation, Pittsburgh, Pa.

[21] Appl. No.: 459,863

[22] Filed: Jun. 2, 1995

[51] Int. Cl.⁶ .................................................. C07C 69/76
[52] U.S. Cl. ........................................ 560/60; 560/221
[58] Field of Search ................................................ 560/140

[56] References Cited

U.S. PATENT DOCUMENTS

| | | | |
|---|---|---|---|
| 3,810,938 | 5/1974 | Schmitt et al. | 560/140 |
| 3,836,576 | 9/1974 | Falize et al. | 260/486 R |
| 3,923,740 | 12/1975 | Schmitt et al. | 560/140 |
| 4,074,062 | 2/1978 | Murakami et al. | 560/217 |
| 4,791,221 | 12/1988 | Gabillet | 560/217 |
| 4,812,591 | 5/1989 | Buysch et al. | 560/140 |
| 4,916,255 | 4/1990 | Kobayashi et al. | 560/217 |

FOREIGN PATENT DOCUMENTS

| | | |
|---|---|---|
| 3215653 | 9/1988 | Japan . |
| 738954 | 10/1955 | United Kingdom . |

*Primary Examiner*—Paul J. Killos
*Attorney, Agent, or Firm*—William L. Krayer; Robert R. Gavlik

[57] ABSTRACT

The present invention relates to a new method of making the dimethacrylate ester of alkoxylated bisphenol-A via transesterification with methyl methacrylate. This transesterification reaction proceeds at low temperatures and is driven by the removal of methanol as a methanol/saturated hydrocarbon azeotrope. The lower temperature reaction advantageously inhibits polyerization of the feed ester. The reaction is catalyzed by potassium based catalysts.

20 Claims, No Drawings

TRANSESTERIFICATION REACTION OF ALKOXYLATED BISPHENOL-A AND METHYL METHACRYLATE

TECHNICAL FIELD

This invention relates to a new method of making the dimethacrylate ester of alkoxylated bisphenol-A; alkoxylated bisphenol-A dimethacrylate. The reaction proceeds at low temperatures by the transesterification of alkoxylated bisphenol-A and methyl methacrylate. The reaction is catalyzed by a basic catalyst, and is driven by the removal of methanol as a methanol/saturated hydrocarbon azeotrope.

BACKGROUND OF THE INVENTION

Transesterification of unsaturated esters is not new to the art. Kobayashi et al, in U.S. Pat. No. 4,916,255, disclose a method for producing transesterification products of methacrylate esters including methyl methacrylate. The reaction takes place in the presence of a lithium catalyst, and temperatures as high as 110° C. to 125° C. Methanol and methyl methacrylate are removed as an azeotrope. Falize et al (U.S. Pat. No. 3,836,576) disclose reaction temperatures in the range of 95° C. to 100° C., and additionally disclose the use of an aromatic polymerization inhibitor.

Gabillet, in U.S. Pat. No. 4,791,221, discloses a process for preparing transesterification products of methyl methacrylate. The reaction takes place in the presence of a lithium catalyst. Here..i the problematic solubility of lithium catalysts is offset by the use of crown ethers and/or cryptands. Reaction temperature are in the range of 100° C. to 140° C., and methanol is removed using a hexane azeotrope.

Murakami et al, in U.S. Pat. No. 4,074,062, disclose a transesterification catalyst consisting of barium, thallium, molybdenum, and/or oxides of these. The process also uses an azeotrope, but focuses on the use of alcohols rather than the alkoxylated diol of applicants' invention.

SUMMARY OF THE INVENTION

The present invention is a new method of making alkoxylated bisphenol-A dimethacrylate ("ABAD") from the transesterification reaction of methyl methacrylate ("MMA") and alkoxylated bisphenol-A ("ABPA"). The transesterification reaction also results in the production of methanol ("MeOH"). The reaction is driven, at least in part, by the removal of MeOH, as it forms, via a MeOH/saturated hydrocarbon azeotrope.

There are many well known saturated hydrocarbons that function effectively as azeotropes with MeOH. They include but are not limited to the following: $C_5$–$C_8$ hydrocarbons, and more preferably $C_6$–$C_7$ hydrocarbons. These alkane azeotropes have the unique feature of azeotroping MeOH without significant co-removal of MMA.

The reaction takes place in the presence of a basic catalyst. Applicants have found potassium alkoxides and hydroxides to be efficient catalysts that are easily removed. Examples of these catalysts include, but are not limited to the following: potassium hydroxide, potassium methoxide, potassium ethoxide, and potassium butoxide. The use of these catalysts is new to the transesterification reaction of ABPA and MMA using a saturated hydrocarbon azeotrope. The potassium catalysts have the unique feature of allowing the reaction to be effectively run at much lower temperatures than prior art processes without compromising reaction rates. This is particularly advantageous because the reaction mixture will polymerize quickly at temperatures above 100° C. Applicants' reaction takes place at temperatures at or below about 100° C. Additionally, applicants have eliminated the need to use cryptands and/or crown ethers. The present reaction can be run at 1 to 5:1 MMA to alcohol equivalents. Typically, the ratio will be about 1.1 to 3.0:1.

DETAILED DESCRIPTION OF THE INVENTION

Applicants have developed a method that maximizes the efficiency at which the transesterification reaction of ABPA and MMA proceeds. The lower temperatures at which applicants' reaction is optimally run at are novel and non-obvious in the art. Polymerization of the ABAD must be avoided to as great an extent as possible. The reaction should be run at as low a temperature as possible. Preferably, the reaction temperature is in the range of about 65° C. to about 100° C., more preferably about 70° C. to about 90° C., and most preferably about 75° C. to about 80° C. The reaction can be run under vacuum, but applicants prefer atmospheric pressure. A polymerization inhibitor may also be employed. These inhibitors are known in the art. Applicants' preferred polymerization inhibitor is selected from the group consisting of hydroquinone, mono-alkoxylated hydroquinone, oxygen containing gases, and non-ionic compounds such as phenothiazine and mixtures thereof.

Applicants note that there are several different ABPA and ABAD molecules. The difference resides in the number of alkoxy groups on each side of the molecule. Applicants preferably use 6-ethoxylated BPA in their reaction. This means ABPA with a statistically distributed total of six alkoxy groups. The ratio of MMA to alcohol is about 1 to about 5:1 equivalents, preferably about 1.1 to about 3.0:1, and most preferably 1.5 to about 2.0:1 equivalents.

Applicants' preferred catalyst is potassium methoxide, but other hydroxides and alkoxides of potassium are effective. It is commonly understood in the art that transesterification catalysts must be added incrementally during the reaction (and removed by filtration). This can be accomplished by any technique in the art. The catalyst is typically added in a weight percent of about 0.04 to about 4.0% of the reaction mixture. Preferably, about 0.2 to about 1.0% is used.

The invention is illustrated by, but not limited to the following examples:

EXAMPLE 1

Into an apparatus consisting of a four-neck, one liter roundbottom flask equipped with a thermowell, agitator, addition funnel/anhydrous air bleed, and a reflux-controlled ten-tray Oldershaw distillation column/cold-water condenser (<10° C.), was added the following materials: 246 g 6-ethoxylated BPA (0.500 mol), 162 g methyl methacrylate (1.62 mol), 0.27 g 4-methoxyphenol (0.11 wt %, based on 6-ethoxylated BPA), 0.27 g phenothiazine (0.11 wt %, based on 6-ethoxylated BPA), 0.15 g potassium methoxide (0.060 wt %, based on 6-ethoxylated BPA), and 21.5 g hexanes (5.00 wt %, based on the reaction charge). The reaction mixture was heated to a moderate boil at atmospheric pressure. After column equilibration was achieved (the column was considered to be equilibrated once the temperature of Oldershaw column tray #5 decreased to its lowest point), distillate was removed at an 8:1 reflux ratio until the temperature on the Oldershaw column tray #5 increased 15° C. above its lowest temperature. The temperature of the reaction mixture was maintained at 80° C. by adding hexanes as needed. The reaction mixture was then cooled to 50° C. and another increment of 0.15 g potassium methoxide catalyst was added. Heating was reinitiated and distillate was collected as before. Repeating the process through two more incremental catalyst additions gave a reaction conversion of 98% (as determined by methanol collection) in 1.5 hours (the total reaction time represents the time of distillate collection). A total of 115 g of hexanes was added to maintain 80° C. Polymer formation was not detected.[1]

[1] The test for polymer formation involved mixing 3 drops of the reaction mixture effluent with approximately 3 g of methanol. Cloudiness or precipitate formation is indicative of polymer formation.

EXAMPLE 2

Into an apparatus consisting of a four-neck, one liter roundbottom flask equipped with a thermowell, agitator, addition funnel/anhydrous air bleed, and a reflux-controlled ten-tray Oldershaw distillation column/cold-water condenser (<10° C.), was added the following materials: 246 g 6-ethoxylated BPA (0.500 mol), 150 g methyl methacrylate (1.50 mol), 0.27 g 4-methoxyphenol (0.11 wt %, based on 6-ethoxylated BPA), 0.27 g phenothiazine (0.11 wt %, based on 6-ethoxylated BPA), 0.15 g potassium methoxide (0.060 wt %, based on 6-ethoxylated BPA), and 20.9 g hexanes (5.00 wt %, based on the reaction charge). The reaction mixture was heated to a moderate boil at atmospheric pressure. After column equilibration was achieved (the column was considered to be equilibrated once the temperature of Oldershaw column tray #5 decreased to its lowest point), distillate was removed at an 8:1 reflux ratio until the temperature on the Oldershaw column tray #5 increased 15° C. above its lowest temperature. The temperature of the reaction mixture was maintained at 75° C. by adding hexanes as needed. The reaction mixture was then cooled to 50° C. and another increment of 0.15 g potassium methoxide catalyst was added. Heating was reinitiated and distillate was collected as before. Repeating the process through three more incremental catalyst additions gave a reaction conversion of 100% (as determined by methanol collection) in 2.4 hours (the total reaction time represents the time of distillate collection). A total of 122 g of hexanes was added to maintain 75° C. Polymer formation was not detected.[1]

[1] The test for polymer formation involved mixing 3 drops of the reaction mixture effluent with approximately 3 g of methanol. Cloudiness or precipitate formation is indicative of polymer formation.

EXAMPLE 3

Into an apparatus consisting of a four-neck, one liter roundbottom flask equipped with a thermowell, agitator, anhydrous air bleed, and a reflux-controlled ten-tray Oldershaw distillation column/cold-water condenser (<10° C.), was added the following materials: 246 g 6-ethoxylated BPA (0.500 mol), 150 g methyl methacrylate (1.50 mol), 0.27 g 4-methoxyphenol (0.11 wt %, based on 6-ethoxylated BPA), 0.27 g phenothiazine (0.11 wt %, based on 6-ethoxylated BPA), 0.15 g potassium methoxide (0.060 wt %, based on 6-ethoxylated BPA), and 105 g heptane (21.0 wt %, based on the reaction charge). The reaction mixture was heated to a moderate boil at a pressure of 550 mm Hg. After column equilibration was achieved (the column was considered to be equilibrated once the temperature of Oldershaw column tray #5 decreased to its lowest point), distillate was removed at an 8:1 reflux ratio until the temperature on the Oldershaw column tray #5 increased 15° C. above its lowest temperature. The temperature of the reaction mixture did not exceed 91° C. The reaction mixture was then cooled to 50° C. and another increment of 0.15 g potassium methoxide catalyst was added. Heating was reinitiated and distillate was collected as before. Repeating the process through three more incremental catalyst additions gave a reaction conversion of 90% (as determined by methanol collection) in 2.4 hours (the total reaction time represents the time of distillate collection). Polymer formation was not detected.[1]

[1] The test for polymer formation involved mixing 3 drops of the reaction mixture effluent with approximately 3 g of methanol. Cloudiness or precipitate formation is indicative of polymer formation.

EXAMPLE 4. Comparative—No Azeotropic Solvent

Into an apparatus consisting of a four-neck, one liter roundbottom flask equipped with a thermowell, agitator, anhydrous air bleed, and a reflux-controlled ten-tray Oldershaw distillation column/cold-water condenser (<10° C.), was added the following materials: 246 g 6-ethoxylated BPA (0.500 mol), 300 g methyl methacrylate (3.00 mol), 0.40 g 4-methoxyphenol (0.16 wt %, based on 6-ethoxylated BPA), 0.40 g phenothiazine (0.16 wt %, based on 6-ethoxylated BPA), and 0.19 g potassium methoxide (0.078 wt %, based on 6-ethoxylated BPA). The reaction mixture was heated to a moderate boil at a pressure of 550 mm Hg. After column equilibration was achieved (the column was considered to be equilibrated once the temperature at Oldershaw column tray #5 decreased to its lowest point), distillate was removed at an 8–10:1 reflux ratio until the temperature on the Oldershaw column tray #5 increased 15° C. above its lowest temperature. The reaction mixture was then cooled to 50° C. and another increment of 0.19 g potassium methoxide catalyst was added. Heating was reinitiated and distillate was collected as before. Repeating the process through two more incremental catalyst additions gave a reaction conversion of 92% (as determined by methanol collection) in 2.3 hours (the total reaction time represents the time of distillate collection). The temperature at the end of the reaction was 104° C. Polymer formation was evident.[1]

[1] The test for polymer formation involved mixing 3 drops of the reaction mixture effluent with approximately 3 g of methanol. Cloudiness or precipitate formation is indicative of polymer formation.

EXAMPLE 5. Comparative—No Azeotropic Solvent/Reduced Pressure

Into an apparatus consisting of a four-neck, one liter roundbottom flask equipped with a thermowell, agitator, anhydrous air bleed, and a reflux-controlled ten-tray Oldershaw distillation column/cold-water condenser (<10° C.), was added the following materials: 246 g 6-ethoxylated BPA (0.500 mol), 300 g methyl methacrylate (3.00 mol), 0.40 g 4-methoxyphenol (0.16 wt %, based on 6-ethoxylated BPA), 0.40 g phenothiazine (0.16 wt %, based on 6-ethoxylated BPA), and 0.19 g potassium methoxide (0.078 wt %, based on 6-ethoxylated BPA). The reaction mixture was heated to a moderate boil at a pressure of 500 mm Hg. After column equilibration was achieved (the column was considered to be equilibrated once the temperature at Oldershaw column tray #5 decreased to its lowest point), distillate was removed at an 8–14:1 reflux ratio until the temperature on the Oldershaw column tray #5 increased 15° C. above its lowest temperature. The reaction mixture was then cooled to 50° C. and another increment of 0.19 g potassium methoxide catalyst was added. Heating was reinitiated and distillate was collected as before. Repeating the process through two more incremental catalyst additions gave a reaction conversion of 89% (as determined by methanol collection) in 2.7 hours (the total reaction time represents the time of distillate collection). The temperature at the end of the reaction was 100° C. Polymer formation was not detected.[1]

[1] The test for polymer formation involved mixing 3 drops of the reaction mixture effluent with approximately 3 g of methanol. Cloudiness or precipitate formation is indicative of polymer formation.

EXAMPLE 6. Comparative Examples 7 and 8 (Different Catalysts)

Example 6 —Into an apparatus consisting of a four-neck, one liter roundbottom flask equipped with a thermowell, agitator, anhydrous air bleed, and a reflux-controlled ten-tray Oldershaw distillation column/cold-water condenser (<10° C.), was added the following materials: 246 g 6-ethoxylated BPA (0.500 mol), 150 g methyl methacrylate (1.50 mol), 0.27 g 4-methoxyphenol (0.16 wt %, based on 6-ethoxylated BPA), 0.27 g phenothiazine (0.16 wt %, based on 6-ethoxylated BPA), 0.15 g potassium methoxide (0.060 wt %, based on 6-ethoxylated BPA), and 105 g hexanes (20.9 wt %, based on the reaction charge). The reaction mixture was heated to a moderate boil at atmospheric pressure. After column equilibration was achieved (the column was considered to be equilibrated once the temperature at Oldershaw column tray #5 decreased to its lowest point), distillate was removed at an 8:1 reflux ratio until the temperature on the Oldershaw column tray #5 increased 15° C. above its lowest temperature. The reaction mixture was then cooled to 50° C. and another increment of 0.19 g potassium methoxide catalyst was added. Heating was reinitiated and distillate was collected as before. Repeating the process through one more incremental catalyst additions gave a reaction conversion of 81% (as determined by methanol collection) in 2.0 hours (the total reaction time represents the time of distillate collection). The temperature at the end of the reaction was 79° C. Polymer formation was not detected.[1]

[1] The test for polymer formation involved mixing 3 drops of the reaction mixture effluent with approximately 3 g of methanol. Cloudiness or precipitate formation is indicative of polymer formation.

Comparative Example 7

The above procedure was repeated substituting lithium methoxide catalyst for potassium methoxide. A conversion of 60% (as determined by methanol collection) was obtained in 2.2 hours (the total reaction time represents the time of distillate collection) with no detectable polymerization.[1] The final reaction temperature was 81° C.

[1] The test for polymer formation involved mixing 3 drops of the reaction mixture effluent with approximately 3 g of methanol. Cloudiness or precipitate formation is indicative of polymer formation.

Comparative Example 8

The above procedure was repeated substituting potassium hydroxide catalyst for potassium methoxide. A conversion of 43% (as determined by methanol collection) was obtained in 1.2 hours (the total reaction time represents the time of distillate collection) with no detectable polymerization.[1] The final reaction temperature was 77° C.

EXAMPLE 9

A pilot-plant apparatus consisting of a 25-gallon, jacketed, glass-lined reactor, a packed column about 4 inches diameter and 4 feet tall, a condenser piped to both ambient and chilled cooling water, a decanter with sight glass, a reflux pump, and a cartridge filter was used. The reactor was charged with recycle material recovered from the preceding run and consisted of 46 grams (g) of methanol, 2413 g of hexane, and 1660 g of methyl methacrylate (MMA). To this were added fresh feeds as follows: 12.15 kg of 6-ethoxylated BPA, 7.98 kg MMA, 1.5 kg of hexane, 23 g of phenothiazine (PTZ), 23 g of methoxyphenol, and 10 g of potassium methoxide (KOCH3). About 2,000 g of recycle (93 wt %) hexane was added to the decanter. The reaction mixture was heated by steam in the reactor jacket to boiling at atmospheric pressure, which occurred at about 75° C. Liquid condensate was allowed to collect in the decanter until the level was above the side take-off to the reflux pump. The reflux pump was then turned on and valves regulated to send liquid flow back to the top of the column such that the liquid level stayed relatively constant at about 5 liters and the reactor temperature at around 75° C.

As the reaction proceeded, methanol was formed as a by-product and distilled out of the reactor along with the hexane. The methanol formed a methanol-rich phase in the separator that was about 63 wt % methanol, 34% hexane, and 3% MMA. The quantity of this phase indicates the progress of the reaction, and it is allowed to accumulate in the decanter until the reaction is deemed to be completed or until the level approaches the overflow to the reflux pump. During the course of the reaction, three additional potassium methoxide catalyst additions were made at about 50-minute intervals as a slurry of about 9 grams of catalyst in 70 ml of methanol.

In this example, about 2.4 kg of methanol-rich phase was removed followed by 1.6 kg of hexane-rich layer after reacting for less than 4 hours. The methanol recovery corresponds to about 99% conversion. Then under slight vacuum (580 mm Hg absolute), approximately 2.2 kg of additional hexane was boiled out and retained for the next batch. The vacuum was then increased gradually down to an absolute pressure of about 60 mm Hg to boil out most of the excess MMA as the temperature was raised to 90° C. Next, about 300 ml of warm water was gradually added below the surface of the agitated reactor contents to effectively steam strip out nearly all the remaining MMA. Finally, the stripped product was pushed through a cartridge filter using about 18 psig of nitrogen pressure to produce the final product. The final product analysis by HPLC indicated no detectable residual MMA and about 99% esters with the ratio of diester to monoester in excess of 7.

We claim:

1. A method of making alkoxylated bisphenol-A dimethacrylate, comprising the steps of:
   (a) combining (i) alkoxylated bisphenol-A, and (ii) methyl methacrylate;
   (b) reacting said combined compounds in the presence of a basic catalyst comprising a compound selected from the group consisting of alkoxides and hydroxide of potassium, wherein the transesterification products alkoxylated bisphenol-A dimethacrylate and methanol are formed; and
   (c) removing methanol with a saturated hydrocarbon azeotrope.

2. The method of claim 1 comprising the further step of separating the methanol and saturated hydrocarbon from the azeotrope mixture.

3. The method of claim 1 wherein the alkoxylated bisphenol-A is 6-ethoxylated bisphenol-A.

4. The method of claim 1 wherein the basic catalyst is selected from the group consisting of potassium hydroxide, potassium methoxide, potassium ethoxide, and potassium butoxide.

5. The method of claim 1 wherein the basic catalyst is potassium methoxide.

6. The method of claim 1 wherein the ratio of (ii) to (i) about 1 to about 5:1.

7. The method of claim 1 wherein the ratio of (ii) to (i) is about 1.1 to about 3.0:1.

8. The method of claim 1 wherein the ratio of (ii) to (i) is about 1.5 to about 2.0:1.

9. The method of claim 1 wherein the reaction takes place at about 100° C. or less.

10. The method of claim 1 wherein the reaction takes place at about 65° C. to about 100° C.

11. The method of claim 1 wherein the reaction takes place at about 70° C. to about 90° C.

12. The method of claim 1 wherein the reaction takes place at 75° C. to about 80° C.

13. The method of claim 1 comprising the further step of adding a polymerization inhibitor in step (b).

14. The method of claim 13, wherein the inhibitor is selected from the group consisting of hydroquinone, monoalkoxylated hydroquinone, phenothiazine, and mixtures thereof.

15. The method of claim 13 wherein the inhibitor comprises a mixture of 4-methoxyphenol and phenothiazine.

16. The method of claim 1 wherein the saturated hydrocarbon is selected from the group consisting of $C_5$ to $C_8$ hydrocarbons.

17. The method of claim 1 wherein the saturated hydrocarbon is selected from the group consisting of $C_6$ and $C_7$ hydrocarbons.

18. The method of claim 1 wherein the saturated hydrocarbon is hexane.

19. The method of claim 1 wherein the amount of catalyst is about 0.04 to about 4.0 wt % of (i).

20. The method of claim 1 wherein the amount of catalyst is about 0.02 to about 1.0 wt % of (i).

* * * * *

UNITED STATES PATENT AND TRADEMARK OFFICE
CERTIFICATE OF CORRECTION

PATENT NO. : 5,567,838
DATED : October 22, 1996
INVENTOR(S) : Pugach et al.

It is certified that error appears in the above-identified patent and that said Letters Patent is hereby corrected as shown below:

In column 1, line 30, delete-- "i"--.
    Title page, item [57],
    In the Abstract, next to last line "polyerization" spelled incorrectly, should read "polymerization".

Signed and Sealed this

Eleventh Day of February, 1997

*Attest:*

BRUCE LEHMAN

*Attesting Officer*     *Commissioner of Patents and Trademarks*